US00PP18385P3

(12) United States Plant Patent
Larsen

(10) Patent No.: US PP18,385 P3
(45) Date of Patent: Jan. 1, 2008

(54) ***OSTEOSPERMUM* PLANT NAMED 'SUNNY DARK AMANDA'**

(50) Latin Name: *Osteospermum ecklonis*
Varietal Denomination: Sunny Dark Amanda

(75) Inventor: Bjarne N. Larsen, Odense (DK)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/412,505

(22) Filed: Apr. 27, 2006

(65) Prior Publication Data

US 2007/0256205 P1 Nov. 1, 2007

(51) Int. Cl.
*A01H 5/00* (2006.01)

(52) U.S. Cl. ..... Plt./360

(58) Field of Classification Search ..... Plt./360
See application file for complete search history.

*Primary Examiner*—Kent Bell
*Assistant Examiner*—Annette H Para

(57) ABSTRACT

A new and distinct cultivar of *osteospermum* plant named Sunny Dark Amanda, particularly characterized by its intense yellow-gold ray-floret color, with the floret tips' being a slightly darker yellow, upright growth habit, elliptic ray florets in one or two complete whorls, and its nonvariegated leaves.

1 Drawing Sheet

The present invention relates to a new and distinct cultivar of *Osteospermum* plant, botanically known as *Osteospermum ecklonis,* and referred to by the varietal denomination 'Sunny Dark Amanda'.

The new cultivar is the product of a planned breeding program carried out by the inventor in Odense, Denmark. The objective of the breeding program was to create new *osteospermum* cultivars with distinctly new inflorescence colors.

The new cultivar originated from a cross made by the inventor in Odense, Denmark, in May 2002. The female, or seed parent, was the cultivar 'Sunny Serena', disclosed in U.S. Plant Pat. No. 15,693, and primarily characterized by its compact, upright, mounded-plant habit, its dense and bushy growth habit, its freely flowering habit, and its pale yellow ray florets and contrasting grey disc florets. The male or pollen parent was an unnamed and unpatented proprietary seedling identified by the code number 30.013.01. The characteristics of the male parent are not presently available.

The first act of asexual reproduction of the new cultivar was accomplished when vegetative cuttings were made from the selection in April 2004 in a controlled environment in Odense, Denmark, by or under the supervision of the inventor.

The new cultivar has not been observed under all possible environmental conditions. The phenotype may vary significantly with variations in environment, such as temperature, light intensity, and day length without, however, any variance in genotype.

SUMMARY OF THE INVENTION

The following traits have been repeatedly observed and have been determined to be basic characteristics of the new cultivar, which in combination distinguish the new cultivar as being new and distinct:

1. The new cultivar has an upright growing habit, and possesses many of the growth characteristics of the female parent 'Sunny Serena'.

2. Nonvariegated leaves.
3. Elliptic ray florets formed in one or two complete ray floret whorls.
4. The mature upper surface ray floret base color is a very deep yellow (13B), with the ray-floret tips being even a more intense deep yellow (13A).

Of the many commercial cultivars known to the present inventor(s), the most similar cultivar in comparison to the new cultivar is the female parent 'Sunny Serena'. The primary distinction is in ray floret color, with the base color of the upper surface of mature ray florets of 'Sunny Serena' being a much lighter yellow, merging into and becoming white at the base. In addition, the mature disc florets of 'Sunny Serena' are gray compared to the mature brown (200C) disc florets of 'Sunny Dark Amanda'.

BRIEF DESCRIPTION OF THE PHOTOGRAPHS

The photograph at the bottom of the sheet shows a front perspective view of typical flowering plants (three) of the new cultivar in an 8" pot. The photograph at the top of the sheet is a view showing in more detail partially and fully open inflorescences of the new cultivars.

The colors in the photographs are as true as is reasonably possible with colored reproductions of this type. If any differences exist between the photographic color and the color values described below, the values in the detailed description are accurate.

DETAILED BOTANICAL DESCRIPTION

In the following description, color references are made to The Royal Horticultural Society Colour Chart. The values are based on plant material grown in Bonsall, Calif., with the plants' being very mature and approximately 20 weeks old.

Botanical classification: *Osteospermum ecklonis* cv 'Sunny Amanda'.

Parentage:

*Female parent.*—'Sunny Serena'.

*Pollen parent.*—A proprietary cultivar identified as 30.013.01.

Propagation:

*Type.*—Terminal vegetative cuttings.

*Time to initiate roots.*—About 10 to 14 days at 18–20 degrees C.

*Root description.*—Fine, fibrous, and branching.

Plant description:

*General appearance and shape.*—Generally V-shaped profile with a very uniform, rounded canopy.

*Habit.*—Fairly loose, open, very good vigor, and very free-branching.

*Plant height.*—37 cm.

*Plant diameter or area of spread.*—40 cm. to 46 cm.

*Lateral branching.*—Number of primary lateral branches: 4.

*Number of secondary lateral branches.*—6–7.

*Length of primary branches.*—About 34 cm. to 36 cm.

*Diameter.*—About 0.6 cm. to 0.7 cm.

*Internode length.*—About 1.0 cm. to 1.3 cm.

*Texture.*—Pubescent.

*Color.*—146 B.

*Foliage.*—Arrangement: Alternate. Simple or Compound: Simple. Length: About 3.8 cm. to 5.0 cm. Width: About 1.6 cm. to 2.4 cm., becoming smaller toward tip. Shape: Oblanceolate to obovate. Apex shape: Broadly acute. Base shape: Attenuate. Margin: Nearly entire but having irregular points. Texture: Top is slightly course, and bottom is minutely pubescent. Color: Developing foliage: Upper surface, 147A. Lower surface, 146A. Mature foliage: Upper surface, 147A. Lower surface, slightly darker than 147B. Venation, upper and lower surfaces: 147A to 147C. Petiole: Length, 1.1 to 1.3 cm. Diameter, 0.4 cm. Color: Both upper and lower sections, 146A. Other foliage characteristics: Dominant midvein, arcuate veins. No distinct petiole. Leaves are tough and leathery.

*Inflorescence.*—Appearance: Solitary, terminal, and axillary. Form: Single daisy, actinomorphic. Orientation: Upright if terminal, outward if axillary. Longevity: 5–6 days. Fragrance: None.

Quantity: About 16 open inflorescences and 28 visible buds on main stem; 4–5 inflorescences and 8 buds on lateral stems, which are oriented about 2 degrees to the vertical.

*Size.*—Total diameter: 6.7 cm. Depth: About 1.5 cm. Diameter of disc: 1.6 cm. Receptacle diameter: 2.0 cm. Receptacle height: 1.0 cm.

*Buds* (*just before anthesis*).—Height: 2.3 cm. Diameter: 1.3 cm. Shape: Ovoid to flat-topped. Color: 200A.

*Ray florets.*—Quantity per inflorescence: 22. Shape: Ligulate. Length: 3.4 cm. Width: 0.7 cm. Apex: Acute and minutely tridentate. Base: Acute. Margin: Entire. Texture: Smooth, satiny. Aspect: Not completely flat; about 75–80 degrees from vertical. Color: When opening: Upper surface ground color is 13B-C, with 17A tips. Lower surface has broad center stripe of 200A-B, with margins' being 17A. Mature: Upper surface, mostly 13B, with 13A tips. Lower surface has 183A-B center stripe, with 17A margins.

*Disc florets.*—Quantity per inflorescence: Approximately 120. Shape: Lanceolate. Apex: Acute, 5 pointed. Base: Truncated. Length: 1.0 cm. Width: 0.2 cm. Color: Immature, 202A. Mature, 200C.

*Involucral bracts.*—Quantity per inflorescence: 19. Length: 1.0 cm. Width: 0.2 cm. Shape: Lanceolate. Apex: Acute. Base: Truncate. Color: Upper surface, 146B. Lower surface, 146A.

*Peduncles.*—Strength: Good. Aspect: Upright to angle of 30 degrees from vertical. Length: Terminal peduncle, 7.2 cm. Fourth peduncle, 3.0 cm. Diameter: About 0.2 cm. Texture: Minutely pubescent. Color: 146B.

*Reproductive organs.*—Androecium: Stamens on disc florets. Stamen number: 5. Anther shape and length: Oblong, 0.2 cm. Anther color: 202A. Pollen color: 23A. Gynoecium: On ray florets only. Pistil length: 0.9 cm. Stigma shape: Bipartite. Stigma color: 200B. Style length: 0.5 cm. Style color: 200C. Seed/fruit: None observed.

Other inflorescence characteristics: Inflorescences partially close at night. As flower ages, ray florets tend to curl backward like black-eyed Susans. Floret rays become lighter as flowers fully open, so that the yellow-gold tips are not as apparent. As the anthers and pollen dehisce from the outer ring toward the center, the pollen shows up as a ring, or bull's eye, until the entire disc shows gold on a black background.

I claim:

1. A new and distinct cultivar of *osteospermum* plant named Sunny Dark Amanda, as illustrated and described.

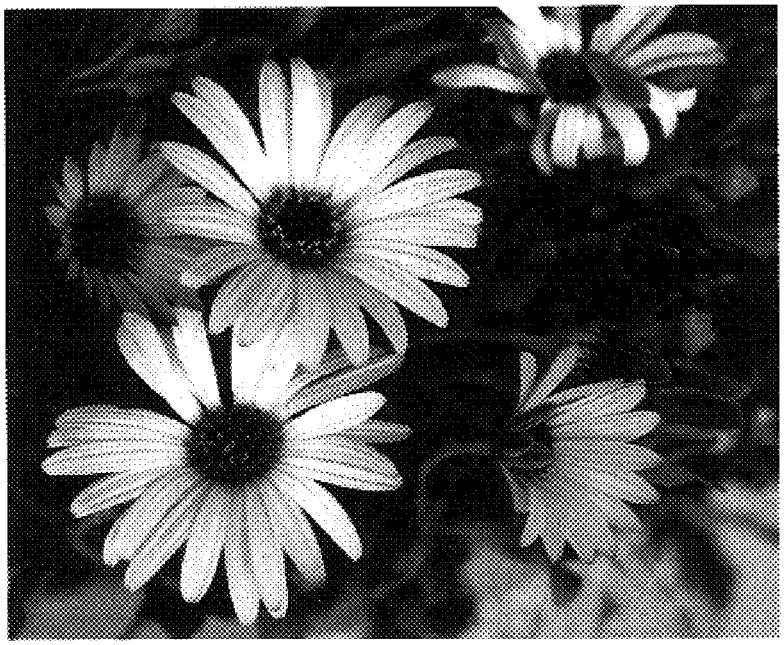
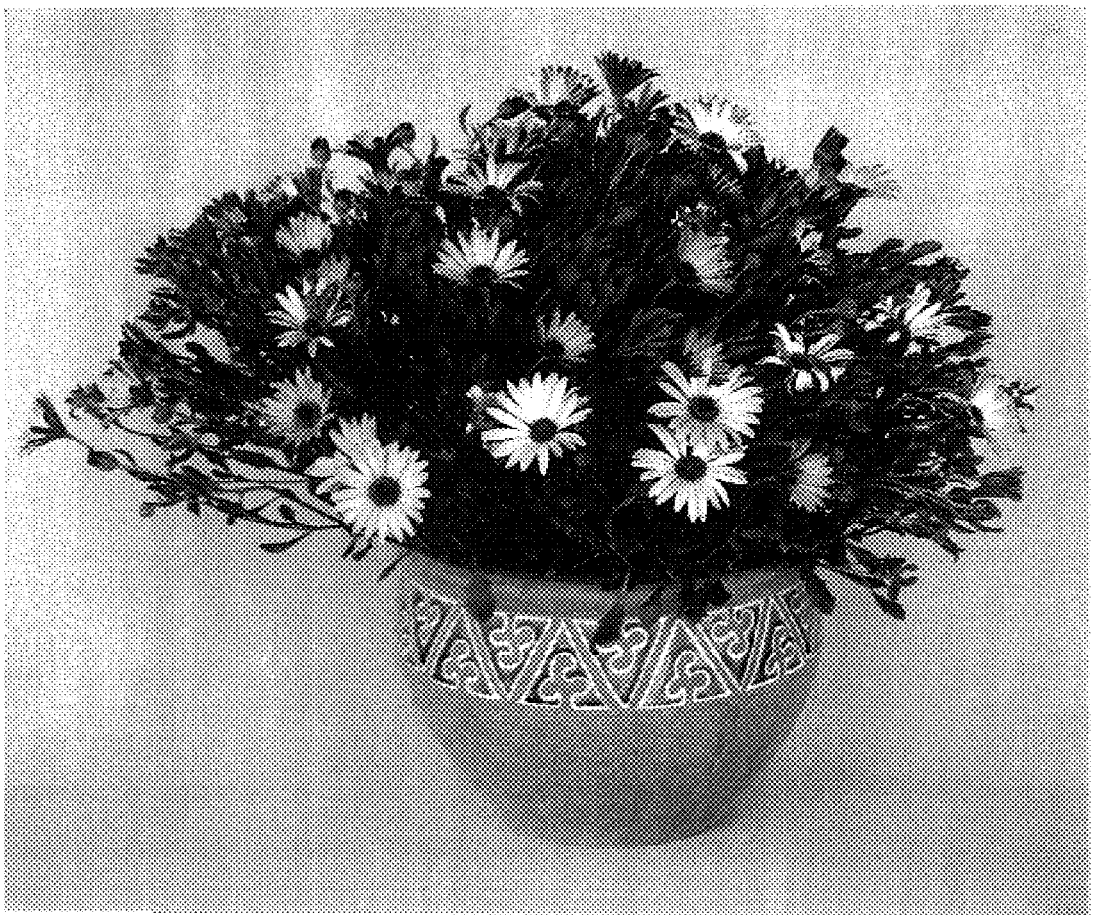

* * * * *